United States Patent [19]

Pez

[11] 4,302,603

[45] Nov. 24, 1981

[54] PRODUCING ALKYLAMINES FROM OLEFINS WITH ALKALI METAL AMIDE CATALYST

[75] Inventor: Guido P. Pez, Boonton, N.J.

[73] Assignee: Allied Chemical Corporation, Morris Township, Morris County, N.J.

[21] Appl. No.: 217,937

[22] Filed: Dec. 18, 1980

[51] Int. Cl.$^3$ ............................................. C07C 85/18
[52] U.S. Cl. ................................... 564/485; 564/445; 423/413
[58] Field of Search ............................... 564/485, 445

[56] References Cited

U.S. PATENT DOCUMENTS

| | | | |
|---|---|---|---|
| 2,501,556 | 3/1950 | Whitman | 260/563 |
| 2,750,417 | 6/1956 | Closson et al. | 260/577 |
| 3,412,158 | 11/1965 | McClain | 260/585 |
| 4,110,377 | 8/1978 | Clerici et al. | 260/583 |

OTHER PUBLICATIONS

W. Howk et al. "Alkali Metal-Catalyzed Amination of Olefins", J.Am. Chem Soc. 1899-1902 (Apr. 5, 1954).
C. A. Kraus et al. "Phase Relationships in the System, Sodium Amide-Potassium Amide," 45 J. Am Chem. Soc. 712-715 (1923).
Kirk-Othmer, Encyclopedia of Chemical Technology, vol. 2, 272-282 (3d Ed. 19).

Primary Examiner—John Doll
Attorney, Agent, or Firm—Alan M. Doernberg; Gerhard H. Fuchs

[57] ABSTRACT

Monolefins such as ethylene are reacted with ammonia using alkali metal amide catalysts such as cesium or rubidium amides, or low melting mixtures of amides such as cesium/potassium, cesium/sodium or sodium/potassium amides. Conversions are improved compared to reactions using sodium or potassium amide alone. Conversions of ethylene are improved also when liquid ammonia is present.

12 Claims, No Drawings

PRODUCING ALKYLAMINES FROM OLEFINS WITH ALKALI METAL AMIDE CATALYST

DESCRIPTION

BACKGROUND OF THE INVENTION

The present invention relates to the production of alkylamines, and particularly to the reaction of monoolefins with ammonia, in the presence of an alkali metal amide catalyst.

Alkylamines having 1-3 alkyls, each with 2-6 carbons, substituted on ammonia are produced commercially by the reaction of an alkanol such as ethanol with either ammonia, a monoalkylamine or a dialkylamine. Since the alkanol is itself normally produced by hydration of an alkene, e.g. the hydration of ethylene to ethanol, the direct production of alkylamines from alkenes would save a step in most commercial operations. In addition, the direct production of alkylamines from alkenes would eliminate the production of water as a by-product, which must be separated from the product alkylamines.

Processes have been proposed for reacting monoolefins with ammonia, monoalkylamines or dialkyamines to produce product alkylamines without the formation of by-products. For example, B. W. Howk et al., in *J. Am. Chem. Soc.*, vol. 76, pp. 1899-1902 (1954) disclose the reaction of ammonia or alkylamines directly with olefins such as ethylene at elevated temperatures and pressures (well above the 132.5° C. critical temperature of ammonia) in the presence of metallic sodium, potassium or lithium, their hydrides or their amides. Temperatures in the range of 175°-200° C. and pressures above 400 atmospheres in the range of 800-1000 atmospheres are indicated. Conversions below 50 percent for reactions with ammonia are indicated under these conditions. Higher conversions are reported for reactions of alkylamines with olefins with similar conditions. The authors support the theory that the reaction proceeds through an anionic mechanism.

For the related reaction of alkylamines with olefins, U.S. Pat. No. 2,750,417 to Closson et al (1956) teaches broadly that inorganic as well as organic amides of alkali metals may be used. Without actual examples other than of sodium amide, this references suggests that the other alkali metal amides (lithium, potassium, rubidium and cesium amides) would also work for this reaction.

U.S. Pat. No. 3,412,158 to McClain (Nov. 19, 1968) discloses the reaction of ethylene with ammonia in the presence of a Group VIII metal catalyst in the vapor phase at a temperature between 90°-175° C. and at a pressure between atmospheric and 2000 psi (100-14,000 kPa), and especially between atmospheric and 100 psi (100-800 kPa). None of these processes, nor any other process using the monoolefin directly, has appeared to supplant the alkanol reaction in commercial operations.

Mixtures of sodium amide and potassium amide are described as having melting points below that of either component, with a 1:2 molar eutectic being disclosed to melt at about 90° C. in J. American Chem. Soc. vol. 45, page 712 (1923).

BRIEF DESCRIPTION OF THE INVENTION

It has been discovered that when the alkali metal amide catalyst used for the direct reaction of a monoolefin with an ammonia to produce alkylamines contains a substantial proportion, e.g. at least 25 mole percent of cesium amide, rubidium amide, or mixtures thereof, or is a mixture of potassium amide with either cesium amide or sodium amide melting below the reaction temperature, a substantial improvement in the conversion to alkylamines is achieved. It has been further discovered that the presence of liquid ammonia in the reaction mixture appreciably increases the reaction rate and conversion, at least when the monoolefin is ethylene.

Accordingly, the present invention includes a process for the production of alkylamines which comprises reacting a monoolefin with ammonia in the presence of an alkali metal amide catalyst wherein the alkali metal amide catalyst is selected from the group consisting of cesium amide, rubidium amide, mixtures of alkali metal amides which are at least 25 mole percent cesium or rubidium amide and mixtures of amides melting below the reaction temperature.

The alkali metal amides may be introduced as such into the reaction mixture or formed in situ. The preferred reaction temperature when ethylene is the reactant is between about 80° C. and about 132.5° C.; and, in that case, the partial pressure of ammonia is preferably sufficient for liquid ammonia to be present.

The present invention also includes novel catalyst compositions which are mixtures of either sodium amide or potassium amide with either cesium or rubidium amide and which melt at least 50° C. below the lower melting of the individual components. Preferred compositions are about 40-85 mol percent cesium amide with about 15-60 mol percent sodium amide and also about 40-70 mol percent cesium amide with about 30-60 mol percent potassium amide.

DETAILED DESCRIPTION OF THE INVENTION

Monoolefins suitable for the present process include cyclic and acyclic alkenes of two to six carbons, which are preferably linear alpha-olefins such as ethylene, propylene, 1-butene, 1-pentene or 1-hexene. Other than ethylene, these olefins form secondary alkylamines such as isopropylamine. Branched alkenes such as isobutylene may also be used. Non-alpha-olefins such as 2-butene or 2-hexene may also be used alone or in admixture with alpha-olefins. Cyclic monoolefins such as cyclohexene may also be used. Ethylene and propylene are the most preferred monoolefin reactants.

The preferred reaction temperature when ammonia and ethylene are the reactants is between about 80° C. and about 132.5° C., the critical temperature of ammonia. The partial pressure of ammonia should then be sufficient to result in the presence of some liquid ammonia at the reaction temperature, and this can be achieved by charging sufficient ammonia to the reaction vessel. A more preferred range for this reaction temperature wikth ethylene is between about 90° C. and about 110° C. Higher temperatures appear to result in some increase of byproduct formation, while lower temperatures reduce the reaction rate. Nevertheless, such higher or lower temperatures are not excluded. In particular, a higher temperature may be more desirable for olefins other than ethylene. When a mixture of amides are used as catalyst, especially for olefins higher than ethylene, a preferred temperature range is about 90° to about 200° C., but higher than the melting point of the mixed amide. A more preferred temperature range for this reaction is between about 100° C. and about 160° C.

The alkali metal amide catalyst used may be one which contains a major proportion of cesium amide, rubidium amide or both (at least 25 mole percent of the total alkali metal amide). It has been found that these amides are more active as catalysts than either sodium or potassium amide. This may be due in part to the high solubility of these amides in liquid ammonia: potassium amide is only moderately soluble in liquid ammonia, and sodium amide is slightly soluble in liquid ammonia. Potassium amide and sodium amide are helpful, at least with cesium amide and probably also with rubidium amide, since a potassium/cesium amide eutectic and a sodium/cesium amide eutectic have been found to exist. Thus any substantial proportion of potassium amide or sodium amide will decrease the melting point of the cesium amide, and will probably have the same effect on rubidium amide. While sodium amide or potassium amide alone are not suitable (and are taught or suggested in the Howk et al article), mixtures of the two, particularly near the 1:2 mole ratio eutectic (melting point about 90° C.) are suitable for the present process. These melts may be used with or without liquid ammonia present. Especially if liquid ammonia is not present, use of low melting amide mixtures are especially preferred.

These mixed amides may be from one of the following systems:
sodium/potassium amide
sodium/cesium amide
potassium/cesium amide
sodium/rubidium amide
potassium/rubidium amide and should melt at least 50° C. below the melting point of the lowest melting component, and below the reaction temperature. It is also contemplated to use a mixture of more than two amides having a melting point at least 50° C. below the melting point of the lowest melting component, and below the reaction temperature. Preferred mixtures are those melting below 150° C. such as sodium/cesium amide mixtures of about 15–50 mole % sodium, potassium/cesium amide mixtures of about 30–60 mole % potassium and sodium/potassium amide mixtures of about 30–70 mole % sodium. Mixtures in these families having at least about 25 mole %, and preferably at least 50 mole % cesium are more preferred since cesium amide is the most active catalyst of the group sodium, potassium and cesium amide. Similar mixtures high in rubidium, if they melt at least 50° C. below the lowest melting component, are also preferred.

Such materials as the alkaline earth amides, for example magnesium, calcium, strontium and barium amides and certain lanthanide (rare-earth) metal amides specifically europium and ytterbium amides may be soluable in the alkali metal mixed amide melts. It is contemplated that mixtures of one or more of the above alkaline earth and/or rare earth amides with the mixed alkali metal amides may also be used as catalysts in this invention.

When liquid ammonia is present, the preferred amides are cesium amide alone, rubidium amide alone and cesium/potassium amide.

The total pressure of the reaction mixture in the present reaction is important but not critical, and is determined by the amount and volatility of the reactants and the temperature and reactor volume. Increased pressures of either ammonia or olefin do tend to increase the reaction rate for a particular olefin and temperature and catalyst. Total pressures above about 1 MPa are preferred, with total pressures between about 8 and about 25 MPa being more preferred.

Since the monoolefin reactant (at least ethylene and propylene) is generally found principally in the vapor or gas phase under reaction conditions, its vapor pressure will be a function of the reaction temperature, the particular olefin and the amount of olefin to be introduced into the reaction mixture. The partial pressure of ammonia will also be a function of the reaction temperature, the amount and identity of olefin and the amount of ammonia introduced. It is preferred when ethylene is the olefin to use sufficient ammonia for liquid ammonia to be present in the reaction mixture, and thus for the partial pressure of ammonia to be high enough to assure that liquid ammonia is present. Reaction will occur even if the temperature is too high or if the ammonia partial pressure is too low for liquid ammonia to be present, but the conversions and rates are substantially increased for ethylene when liquid ammonia is present. It is then preferred that sufficient liquid ammonia be present to dissolve part, or more preferably all, of the alkali metal amide catalyst. In the case of cesium amide or rubidium amide alone, this amount is a function of temperature and the known solubility limits. In the case of the potassium/cesium amide system, the sodium/cesium amide system and the potassium/sodium amide system, the melts of amides are expected to be miscible in all proportions with liquid ammonia, and thus any amount of liquid ammonia may be beneficial.

EXAMPLE 1

A stainless steel pressure vessel equipped with magnetic stirrer was connected to a pressure gage (of minimal internal volume) to produce a system of about 40 mL internal volume. The vessel was loaded with cesium amide (1.5 g, 10.1 mmol), anhydrous ammonia (237 mmol) and ethylene (132 mmol). The amide was transferred and loaded in an inert atmosphere because it is hydroscopic in air. The gases were charged using a metal pressure/vacuum gas manifold. The full length of the reactor was heated with stirring to 101° C. and kept at that temperature for one hour. Then the reactor contents were bled into a liquid nitrogen-cooled trap and the pressure, if any, from residual non-condensible gases (nitrogen and hydrogen) was read on a mercury manometer. In this example about 0.04 mmol of nitrogen and hydrogen was seen. The condensed liquid was distilled at −111° C. to remove the bulk of the unreacted ethylene, with the gas removed analyzed for ethane (detection limit about 0.1 mmol). In this example no ethane was seen. The removed liquid product was analyzed by gas chromatography, using calibrations with known mixtures of ammonia, mono-, di-, and triethylamine. In this Example, the products were monoethylamine (MEA) (32 mmol), diethylamine (DEA) (3 mmol) and triethylamine (TEA) (2 mmol), for 34% conversion to alkylamines based on ethylene, the limiting reactant in this example. No other organic products were detected by gas chromatography.

EXAMPLE 2–9

Example 1 was repeated with the variations in catalyst and time (at 101° C.) indicated in Table 1. In all cases 132 mmol ethylene and 237 mmol ammonia were charged. For Example 6, the catalyst from Example 4 wa left in the reactor. The pressure when 101° C. was first reached and at the end of the reaction period are indicated. The amounts of various ethylamines (MEA, DEA and TEA) detected are shown in Table 1, as are the calculated conversions of ethylene.

TABLE 1

| | | MNH₂ Catalysts at 101° C. | | | | | |
|---|---|---|---|---|---|---|---|
| Ex | Hours at 101° C. | Pressure Start/Stop MPa | M | mmol | MEA mmol | DEA mmol | TEA mmol | Conversion % |
| 1 | 1 | 11.3/9.3 | Cs | 10.1 | 32 | 3 | 2 | 34 |
| 2 | 1.5 | 11.4/9.2 | Cs | 6.7 | 28 | 3 | 1 | 28 |
| 3 | 3 | 11.2/9.0 | Rb | 9.6 | 34 | 3 | 0.7 | 32 |
| 4 | 1 | 11.9/10.6 | Cs K | 5.1 4.4 | 21 | 2 | 1 | 21 |
| 5 | 3 | 11.2/8.5 | Cs K | 5.1 4.4 | 32 | 3 | 2 | 33 |
| 6 | 6 | 11.9/7.0 | * | * | 59 | 9 | 4 | 67 |
| C7 | 16.5 | 11.4/** | Na | 18.2 | 2 | — | — | 1.4 |
| C8 | 20.5 | 11.4/11.4 | K | 9.4 | 1.6 | 0.1 | — | 1.4 |
| 9 | 19 | 12.0/9.7 | K Na | 11.3 22.8 | 26 | 1 | — | 21 |

*The catalyst for Example 6 was the used catalyst from Example 4.
**In Comparative Example 7, the pressure at the end of the reaction was not measured.

No ethane or non-condensibles were detected in Examples 2, 3, 4 or 5 or in Comparative Examples 7 and 8, with detection limits being about 0.04 mmol for non-condensible and 0.1 mmol for ethane. In Example 1, 0.04 mmol of non-condensibles (the detection limit) was detected, but no ethane. In Examples 6 and 9, respectively, 2 and 0.3 mmol of ethane and 0.4 and 1 mmol of non-condensibles were detected.

These results show high conversions in short times for cesium amide (1 and 2), rubidium amide (3) and the cesium/potassium amide melt (4 and 5). Sodium (C7) or potassium (C8) amide alone produced very small yields even after extended periods. The sodium/potassium amide eutectic (9) produced better yields, but only after an extended period.

EXAMPLE 10—111° C.

Example 1 was repeated using 2.7 mmol of cesium amide at 111° C. for 1.1 h. The products were MEA (17 mmol), DEA (1 mmol) and TEA (0.7 mmol) with no ethane and about 0.2 mmol non-condensibles detected. This represents a 16% conversion with less catalyst, higher temperature and a shorter reaction time, but at the expense of formation of a small amount of hydrogen and nitrogen non-condensible by-products.

EXAMPLE 11—80° C.

When Example 4 was repeated at 80° C. over 16 h, but with less ammonia (167 mmol) and ethylene (113 mmol), conversion to MEA, DEA and TEA was observed, with small amounts of ethane and noncondensibles detected. Other runs showed pressure drops, indicative of reaction occurring, with temperatures as low as 80° C. and as high as 120° C.

EXAMPLE 12—Propylene Amination With Cesium Amide

A reactor of approximately 40 mL internal volume was loaded with cesium amide (1.4 g), ammonia (237 mmol) and propylene (168 mmol). The reactor was heated with magnetic stirring at 111° C. for two hours and then at 116° C. for 19 hours. At the latter temperature the pressure was 12.4 MPa. It is believed that under these conditions the CsNH₂ is (at least in part) dissolved in liquid NH₃. A small pressure drop of about 0.06 MPa was noted during the reaction period. The reactor contents were then bled into a −196° C. cold trap, and the presence of any non-condensibles (none were found in this case) were measured on a mercury manometer. The product was fractionated at low temperatures (−80° C.) into (a) a mixture of largely propylene with some ammonia and (b) a mixture of ammonia and propylamines. The fraction (a) was analyzed by gas chromatography for propylene and propane. No propane was found in this example. Fraction (b) was shown by gas chromatography to contain isopropylamine (about 10 mmol) and n-propylamine (about 0.4 mmol).

EXAMPLE 13

A 40 mL reactor was loaded with 2.5 g of a mixture of cesium and potassium amides (ratio Cs (metal): K(metal)=4:1 by weight), ammonia (118 mmol) and propylene (142 mmol). The mixture was heated with stirring for 17 hours at 139° C. During this period, the pressure dropped from approximately 12.1 to 11.2 MPa. The products: isopropylamine (19 mmol) and n-propylamine (about 0.8 mmol) were collected, as detailed in Example 12. In this example, however, small amounts of non-condensible gases (hydrogen and nitrogen) and some propane were also formed.

EXAMPLE 14

A pressure reactor of about 40 mL capacity was charged with a mixture of cesium amide (2.75 g) and sodium amide (0.25 g). Ammonia (122 mmol) and propylene (142 mmol) were then condensed into the reactor. The mixture was heated, with magnetic stirring, to 139° C. for 17.5 hours. The apparatus was then cooled to about 120° C. and all the volatiles collected and fractionated in vacuum, as detailed in Example 13. Isopropylamine (13 mmol), n-propylamine (0.7 mmol) were formed. Propane (2 mmols) and non-condensible gases (0.8 mmols) were also produced.

EXAMPLE 15—Freezing Points Cesium/Potassium Amide and Cesium/Sodium Amide

Cesium amide was mixed with sodium amide in the proportions, by weight, indicated in Table 2. Cesium amide was mixed with potassium amide in the proportions, by weight, indicated in Table 3. The compositions were melted under an inert atmosphere and allowed to cool slowly with temperature monitoring. Inflections at the freezing points indicated in the tables were observed. It should be noted that all mixtures measured melted well below the melting point of pure cesium amide (262° C.), pure potassium amide (338° C.) or pure sodium amide (210° C.).

TABLE 2

| | Cesium/Sodium Amide | |
|---|---|---|
| Weight Ratio CsNH$_2$/NaNH$_2$ | Mole % NaNH$_2$ | Freezing Point Range |
| 15:1 | 20.2 | 126–128° C. |
| 13:1 | 22.8 | 116–118° C. |
| 11.5:1 | 24.9 | 113–114° C. |
| 9:1 | 28.8 | 115–116° C. |
| 7:1 | 35.1 | 118–119° C. |
| 5:1 | 43.4 | 133–134° C. |

TABLE 3

| | Cesium/Potassium Amide | |
|---|---|---|
| Weight Ratio CsNH$_2$/KNH$_2$ | Mole % KNH$_2$ | Freezing Point Range |
| 10:1 | 21.3 | 173–177° C. |
| 5:1 | 35.1 | 125–130° C. |
| 3.3:1 | 45.0 | 92–93° C. |
| 2.5:1 | 51.9 | 97–98° C. |

What is claimed is:

1. A process for the production of alkylamines which comprises reacting a monoolefin with ammonia in the presence of an alkali metal amide catalyst wherein the alkali metal amide catalyst is selected from the group consisting of cesium amide, rubidium amide, mixtures of alkali metal amides which are at least 25 mole percent cesium or rubidium amide and mixtures of amides melting below the reaction temperature.

2. The process of claim 1 wherein at least 25 mol percent of the alkali metal catalyst is cesium amide.

3. The process of claim 2 wherein the alkali metal catalyst is cesium amide.

4. The process of claim 1 wherein the alkali metal catalyst is a mixture of about 40 to about 70 mol percent cesium amide and about 30 to about 60 mol percent potassium amide.

5. The process of claim 1 wherein the alkali metal catalyst is a mixture of about 40 to about 85 mol percent cesium amide and about 15 to about 60 mol percent sodium amide.

6. The process of claim 1 wherein the alkali metal catalyst is rubidium amide.

7. The process of claim 1 wherein the alkali metal catalyst is a mixture of about 25 to about 40 mol percent potassium amide with about 60 to about 75 mol percent sodium amide.

8. The process of claim 4 or 5 or 7 wherein the reaction temperature is between the melting point of the mixture and 220° C.

9. The process of claim 1 or 2 or 3 or 4 or 5 or 6 wherein the reaction temperature is between about 80° C. and about 132.5° C. and the partial pressure of ammonia is sufficient for liquid ammonia to be present in the reaction mixture throughout the reaction.

10. The process of claim 9 wherein the alkali metal amide is dissolved in liquid ammonia.

11. The process of claim 9 wherein the monoolefin is ethylene.

12. The process of claim 11 wherein the reaction temperature is between about 90° C. and about 110° C.

* * * * *